United States Patent [19]

Markin

[11] Patent Number: 5,567,386
[45] Date of Patent: Oct. 22, 1996

[54] ELEVATOR AND SPECIMAN CARRIER FOR AUTOMATED CONVEYOR SYSTEM

[75] Inventor: Rodney S. Markin, Omaha, Nebr.

[73] Assignee: Board of Regents- Univ. of NE, Lincoln, Nebr.

[21] Appl. No.: 418,942

[22] Filed: Apr. 7, 1995

[51] Int. Cl.$^6$ .................................................. G01N 35/04
[52] U.S. Cl. .......................... 422/65; 422/63; 422/104; 436/43; 436/47; 198/860.1; 198/817
[58] Field of Search ............................... 422/63, 65, 99, 422/100, 102, 103, 104; 436/43, 47; 198/801, 860.1, 817

[56] References Cited

U.S. PATENT DOCUMENTS

| | | | |
|---|---|---|---|
| 3,302,615 | 2/1967 | Tietje | 422/65 |
| 3,371,769 | 3/1968 | Beninger | 198/801 |
| 3,575,692 | 4/1971 | Gilford | 422/65 |
| 3,578,412 | 5/1971 | Martin | 23/259 |
| 3,587,676 | 6/1971 | Oehlin | 422/65 |
| 3,666,082 | 5/1972 | Riggs | 198/130 |
| 3,713,771 | 1/1973 | Taylor et al. | 23/230 R |
| 3,724,654 | 4/1973 | Gerard et al. | 206/459 |
| 3,897,216 | 7/1975 | Jones | 23/259 |
| 3,916,157 | 10/1975 | Roulette et al. | 235/61.12 R |
| 3,986,446 | 10/1976 | Thompson et al. | 198/801 |
| 4,022,579 | 5/1977 | Revillet et al. | 23/259 |
| 4,040,533 | 8/1977 | DeBoer et al. | 214/310 |
| 4,218,534 | 8/1980 | LaBelle et al. | 435/5 |
| 4,303,363 | 12/1981 | Cervin | 414/10 |
| 4,389,374 | 6/1983 | Sutton et al. | 422/102 |
| 4,454,939 | 6/1984 | Kampf et al. | 198/341 |
| 4,482,522 | 11/1984 | Baudisch et al. | 422/104 |
| 4,510,119 | 4/1985 | Hevey | 422/71 |
| 4,534,465 | 8/1985 | Rothermel et al. | 206/443 |
| 4,727,033 | 2/1988 | Hijikata et al. | 436/69 |
| 4,738,824 | 4/1988 | Takeuchi | 422/63 |
| 4,938,369 | 7/1990 | Carilli | 211/74 |
| 5,011,779 | 4/1991 | Maimon | 435/293 |
| 5,021,218 | 6/1991 | Davis et al. | 422/104 |
| 5,069,336 | 12/1991 | Mauthe | 206/219 |
| 5,148,919 | 9/1992 | Rubin | 206/443 |
| 5,158,895 | 10/1992 | Ashihara et al. | 436/526 |
| 5,186,339 | 2/1993 | Heissler | 211/74 |
| 5,217,694 | 6/1993 | Gibler et al. | 422/104 |
| 5,350,564 | 9/1994 | Mazza et al. | 422/63 |
| 5,351,801 | 10/1994 | Markin et al. | 198/364.1 |
| 5,370,215 | 12/1994 | Markin et al. | 198/346.1 |
| 5,417,922 | 5/1995 | Markin et al. | 422/65 |

FOREIGN PATENT DOCUMENTS

| | | |
|---|---|---|
| 3934088 | 4/1991 | Germany . |
| 8300102 | 1/1983 | WIPO . |

*Primary Examiner*—Long V. Le
*Attorney, Agent, or Firm*—Zarley, McKee, Thomte, Voorhees & Sease; Mark D. Frederiksen

[57] ABSTRACT

An elevator for specimen carriers includes an upper housing which is removably connected to an upstream end of an upper conveyor track and a lower housing which is removably connected to a downstream end of a lower conveyor track, the conveyor tracks being vertically spaced. Each conveyor track has a moving support surface which transports a specimen carrier downstream. The elevator includes a pair of opposingly disposed lift pins operably mounted along a chain housed within the elevator, the lift pins located to engage opposingly disposed wings on each specimen carrier, to lift the specimen carrier from the lower track to the upper track. The elevator housings are adjustably connected together, to permit adjustment of the overall height of the elevator for a variety of vertically spaced tracks.

4 Claims, 7 Drawing Sheets

ELEVATOR AND SPECIMEN CARRIER FOR AUTOMATED CONVEYOR SYSTEM

TECHNICAL FIELD

The present invention relates generally to systems for the automation of clinical laboratories and the like, and more particularly to an elevator and specimen carrier utilized with a conveyor track utilized in an automated conveyor system for transporting specimens throughout an automated laboratory.

BACKGROUND OF THE INVENTION

Clinical laboratory testing has changed and improved remarkably over the past 70 years. Initially, tests or assays were performed manually, and generally utilized large quantities of serum, blood or other materials/body fluids. As mechanical technology developed in the industrial work place, similar technology was introduced into the clinical laboratory. With the introduction of new technology, methodologies were also improved in an effort to improve the quality of the results produced by the individual instruments, and to minimize the amount of specimen required to perform a particular test.

More recently, instruments have been developed to increase the efficiency of testing procedures by reducing turnaround time and decreasing the volumes necessary to perform various assays. Present directions in laboratory testing focus on cost containment procedures and instrumentation. Laboratory automation is one area in which cost containment procedures are currently being explored. Robotic engineering has evolved to such a degree that various types of robots have been applied in the clinical laboratory setting.

The main focus of prior art laboratory automation relies on the implementation of conveyor systems to connect areas of a clinical laboratory. Known conveyor systems in the laboratory setting utilize separate conveyor segments to move specimens from a processing station to a specific laboratory work station. In order to obtain cost savings, the specimens were sorted manually, and grouped in a carrier rack to be conveyed to a specific location. In this way, a carrier would move a group of 5–20 specimens from the processing location to the specific work station for the performance of a single test on each of the specimens within the carrier rack.

With the development of new and improved automatic conveyor systems for laboratories and other environments, the inventors herein have found a need for a customized conveyor track and support system for supporting the conveyor track above the ground. Preferably, the track and support system permits flexibility in the arrangement of tracks and "gates" accessing various work stations, as well as simple and economic modules which are easily connected to customize the layout of the particular conveyor system.

In the prior art, conveyor track was conventional directly suspended from a ceiling or a wall support. For this reason, each and every section of conveyor track would necessarily be customized to fit a particular location. In the event of a repair, or other mechanical problem, the entire conveyor track would need to be shut down and the pertinent section removed for repair or replacement. Because of the customized design of each automated conveyor system of the prior art, any replacement pieces would also necessarily be customized.

Prior art elevator systems typically utilized a vertically moveable platform upon which a specimen carrier would rest during transport. However, it has been found that such prior art elevator systems are relatively complex to employ in the automated laboratory conveyor systems currently available, and typically do not provide for enclosed transport to contain any spilled fluid during the movement of a specimen among vertically displaced tracks.

Another problem with prior art elevator systems was in the time required to customize a particular elevator between two vertically displaced tracks. Most elevator systems required that the tracks be spaced a predetermined and uniform distance apart, in order to prevent customized manufacture of an elevator for a particular location. Unfortunately, on site laboratory automation systems frequently require non-uniform movement and locations. Thus, such unified vertical displacement was rarely found in the typical laboratory setting.

A change in the type of elevator utilized in automated conveyor systems also requires the modification of the specimen carrier for use in combination with the elevator.

In the laboratory environment, it is common for the conveyor track to transport various fluid specimens among a plurality of work stations. One problem with prior art designs of conveyor track was in the fact that spillage of such fluid would contaminant the track and the surrounding environment.

SUMMARY OF THE INVENTION

It is therefore a general object of the present invention to provide an improved elevator and specimen carrier for a modular conveyor track in an automated conveyor system.

Another object is to provide an elevator which includes features for the retention of fluid spillage, and to prevent the escape of fluid which has been spilled.

Yet another object of the present invention is to provide an elevator which may be easily connected to a modular conveyor track in an automated conveyor system.

A further object is to provide an elevator which is vertically adjustable in length to extend between a variety of vertically displaced conveyor tracks.

Still another object is to provide an improved specimen carrier which cooperates with an improved elevator to permit simple and efficient vertical transport of the specimen carrier from one conveyor track to a second vertically displaced conveyor track.

These and other objects of the present invention will be apparent to those skilled in the art.

The elevator for specimen carriers of the present invention includes an upper housing which is removably connected to an upstream end of an upper conveyor track and a lower housing which is removably connected to a downstream end of a lower conveyor track, the conveyor tracks being vertically spaced. Each conveyor track has a moving support surface which transports a specimen carrier downstream. The elevator includes a pair of opposingly disposed lift pins operably mounted along a chain housed within the elevator, the lift pins located to engage opposingly disposed wings on each specimen carrier, to lift the specimen carrier from the lower track to the upper track. The elevator housings are adjustably connected together, to permit adjustment of the overall height of the elevator for a variety of vertically spaced tracks.

DESCRIPTION OF THE PREFERRED EMBODIMENT

Figure 1:
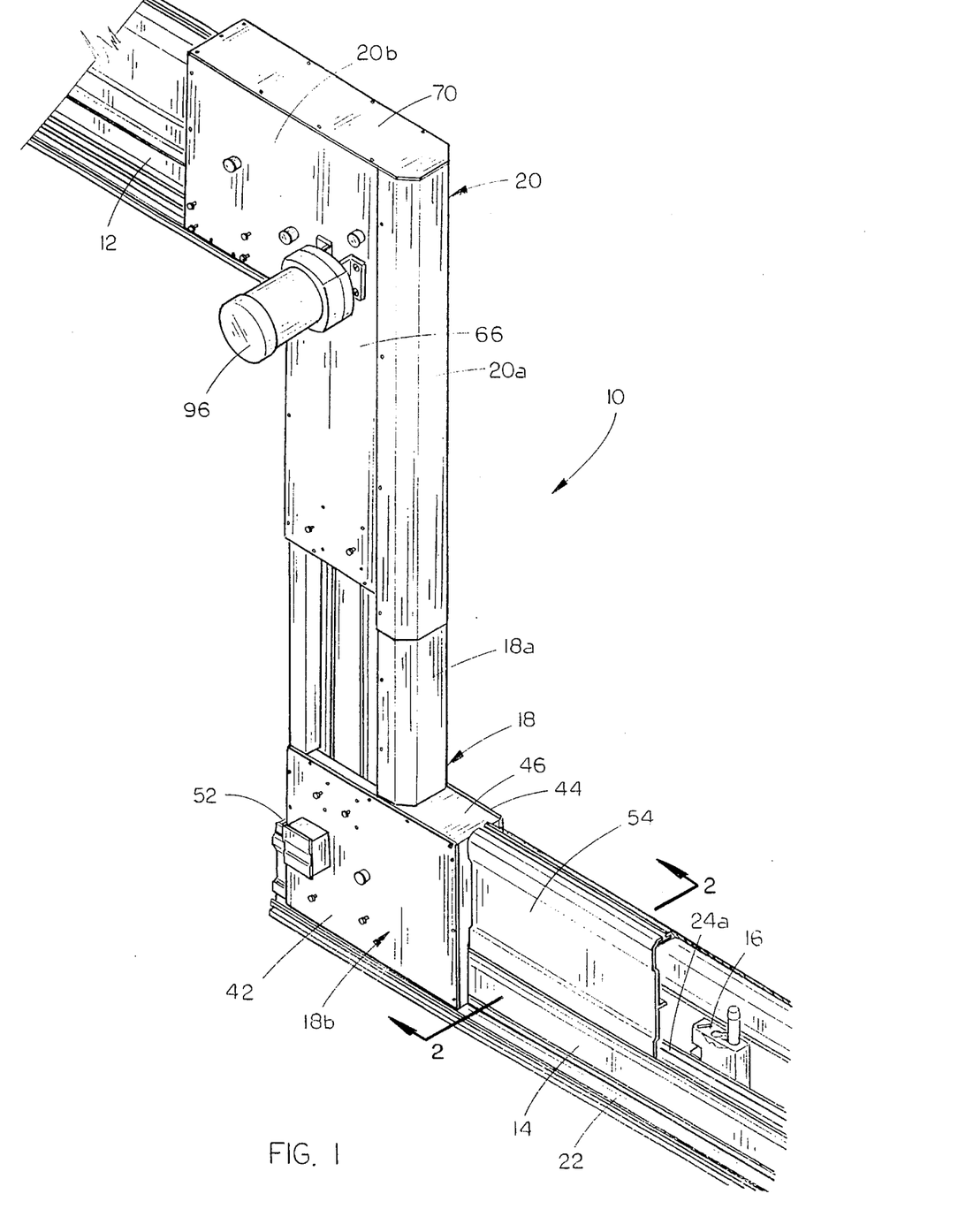
FIG. 1 is a perspective view of the elevator of the present invention installed between an upper and lower conveyor track.

Referring now to the drawings, in which identical or corresponding parts a identified with the same reference numeral, and more particularly to FIG. 1, the elevator of the present invention is designated generally at 10 and is shown connected between an upper conveyor track 12 and a lower conveyor track 14, for the vertical transport of a specimen carrier 16 therebetween.

Elevator 10 includes a lower generally L-shaped housing 18 telescopically connected to an upper inverted L-shaped housing 20, with the vertical back 18a of lower leg 18 inserted within the vertical back 20a of upper housing 20. The horizontal leg 18b of lower housing 18 is secured to lower track 14, while the horizontal leg 20b of upper housing 20 is secured to upper track 12.

Figure 2:
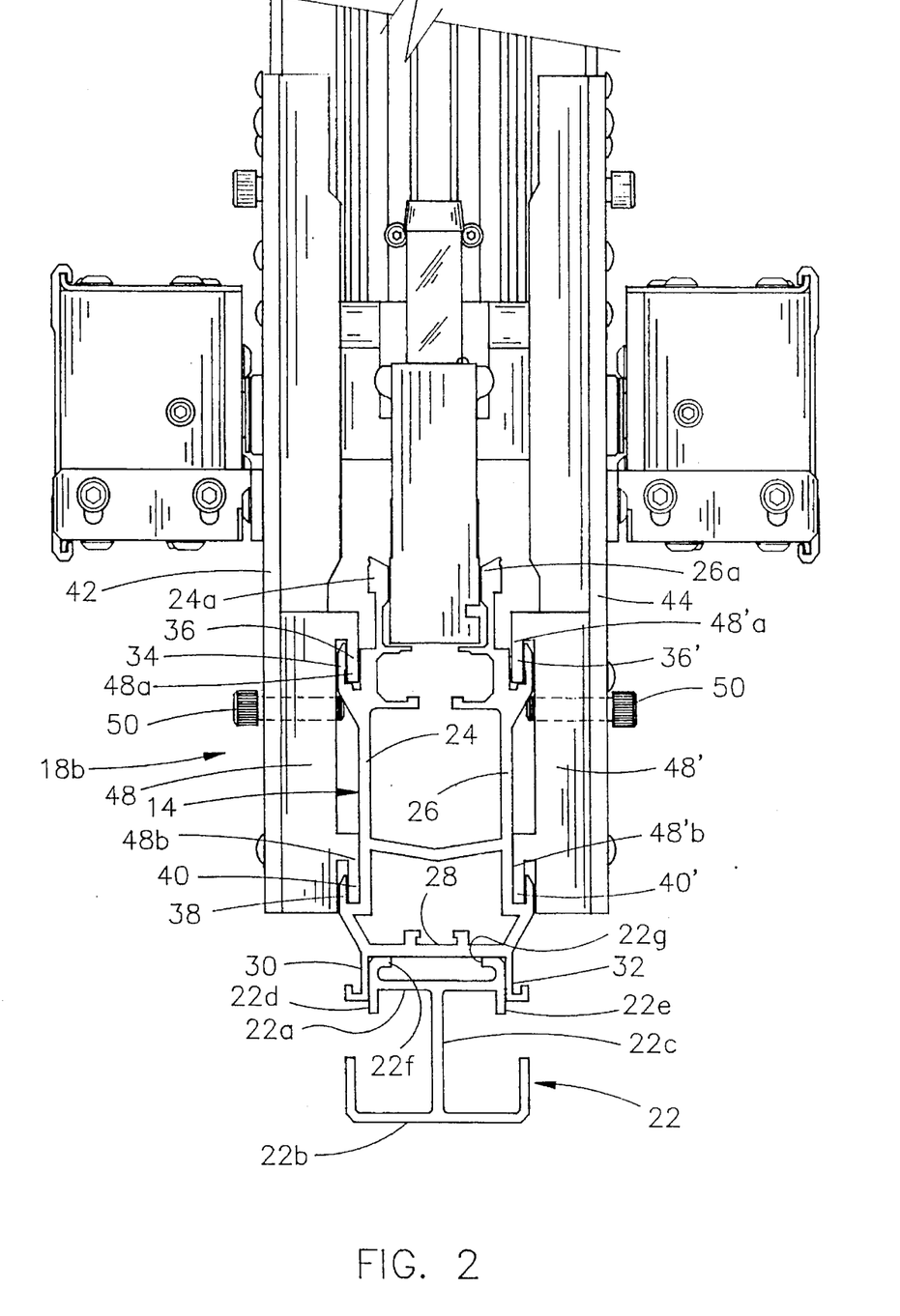
FIG. 2 is an enhanced side elevational view of the elevator lower housing and lower track.

Referring now to FIG. 2, conveyor track 14 is supported on a support rail 22, which is connected to a plurality of hangers to support conveyor track 14 above the ground. Support rail 22 has a generally I-shaped cross-section with an upper horizontal plate 22a connected to a lower horizontal plate 22b by a vertical web 22c. Upper plate 22a includes a pair of upwardly projecting forward and rearward walls 22d and 22e, oriented parallel to web 22c. Upper plate walls 22d and 22e each have an upper lip 22f and 22g, respectively, and inwardly towards one another to form a pair of co-planar horizontal upper support surfaces.

Conveyor track 14 has a generally U-shaped cross-section with a forward vertical leg 24 and a rearward vertical leg 26 connected by a generally horizontal base plate 28. A generally J-shaped fastener leg 30 depends from the lower end of forward leg 24, below base plate 28. A rearward J-shaped fastener leg 32 depends from the lower end of rearward leg 26, below base plate 28, opposite to forward fastener leg 30. Base plate 28 of lower track 14 is supported on the upper support surfaces of lips 22f and 22g of support rail 22, as shown in FIG. 2. Fastener legs 30 and 32 receive the support rail upper walls 22d and 22e therebetween, such that track 14 engages support rail 22. Clips (not shown) interconnect fastener legs 30 and 32 with support rail 22 to securely fasten track 14 to support rail 22.

An upper flange 34 projects forwardly and upwardly from a location spaced below the upper end 24a of track forward leg 24. Upper flange 34 thereby forms an upper support channel 36 between flange 34 and the forward face of forward leg 24. A lower flange 38 also projects forwardly and upwardly from the forward face of forward leg 24, at a position spaced below upper flange 36 and spaced above base plate 28. Lower flange 38 thereby forms a lower support channel 40 on the forward surface of forward leg 24 spaced below upper support channel 36. Rearward leg 26 is a mirror image of forward leg 24, and also includes an upper support channel 36' and lower support channel 40' thereon. As shown in FIG. 2, upper and lower support channels 36, 36', 40 and 40' provide support for lower housing leg 18b, as described in more detail hereinbelow.

Figure 3:
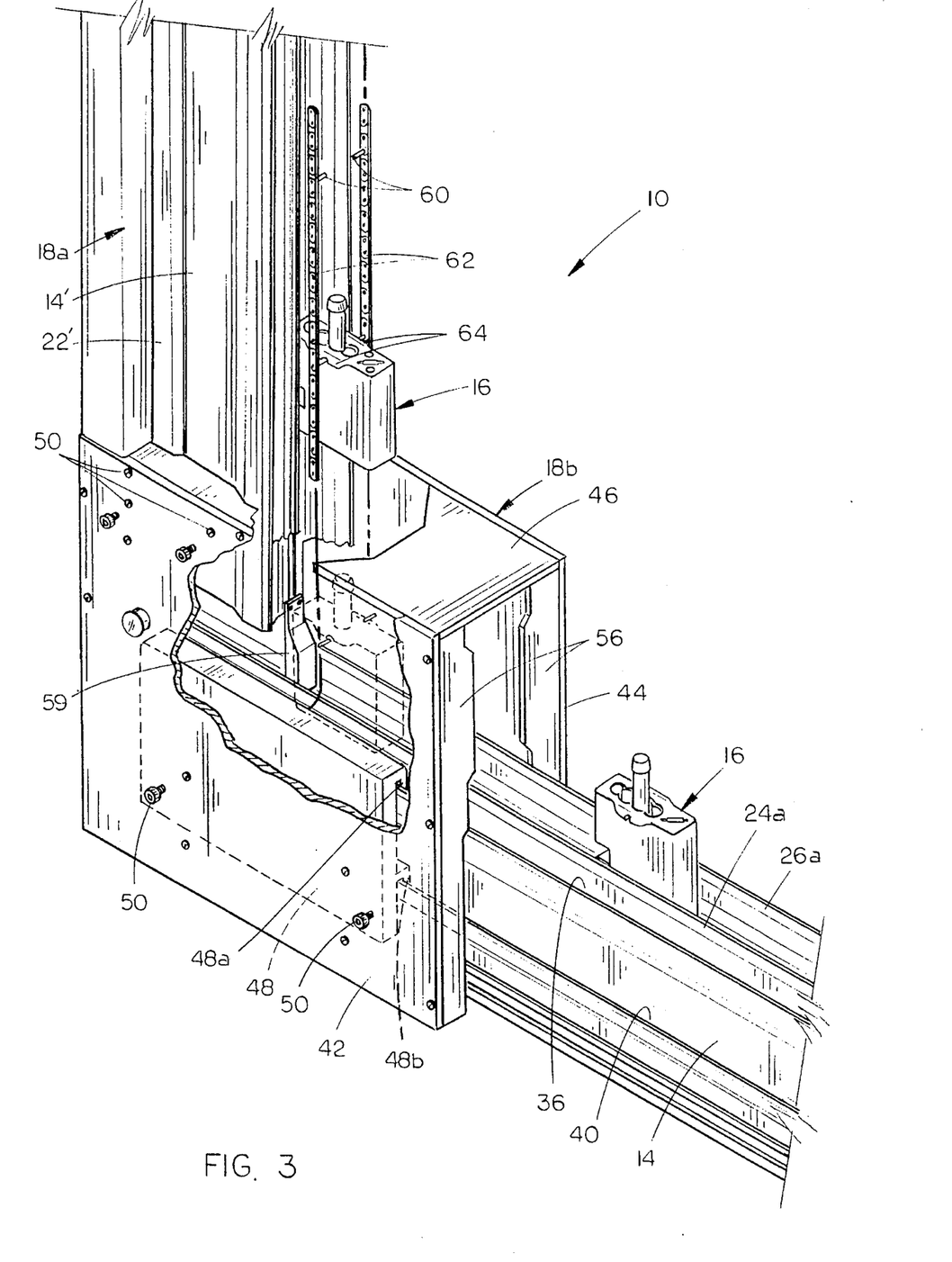
FIG. 3 is an enlarged perspective view of the lower housing of the elevator, with portions broken away for clarity.

Referring now to FIG. 3, lower housing leg 18b includes a pair of forward an rearward opposing parallel plates 42 and 44 connected at their upper ends by a to plate 46, to form a generally inverted U-shaped housing. A pair of hook members 4 are mounted on the inward face of forward plate 42, each hook member 48 having a upper hook 48a and a lower hook 48b projecting inwardly and downwardly from a inward face thereof, for engagement in the upper and lower support channels 36 an 40 of conveyor track 14. A second pair of hook members 48' are mounted on the inward face of rearward plate 44, disposed oppositely of hook members 48, with upper and lower hooks 48'a and 48'b engaged in upper and lower channels 36' and 40', as shown in FIG. 2. Set screws 50, threaded through apertures in forward and rearward plates 42 and 44 engage the sides of track 14 to secure lower housing 18 in position.

Referring once again to FIG. 1, lower track 14 and support rail 22 extend through lower housing 18, to project from the opposite end thereof. An end cap 52 is provided for the end of the projecting conveyor track 14 and support rail 22, and serves to retain any fluids spilled within the conveyor track 14 from escaping from the track.

A removable cover 54 is provided for conveyor track 14, and has a generally inverted U-shape and is preferably formed of a resilient material such as plastic. Cover 54 snaps over the upwardly projecting legs 24a and 26a of conveyor track 14 to form an enclosed housing through which specimen carriers 16 are transported.

Referring once again to FIG. 3, a pair of opposing co-planar end walls 56 are mounted between lower housing forward and rearward plates 42 and 44, with each end wall having an inwardly directed edge with a profile matching the profile of track 14 and the cover 54 (also shown in FIG. 1 ). Thus, specimen carrier 16 remains enclosed as it is transported along conveyor track 14 into lower housing 18 of elevator 10.

Figure 4:
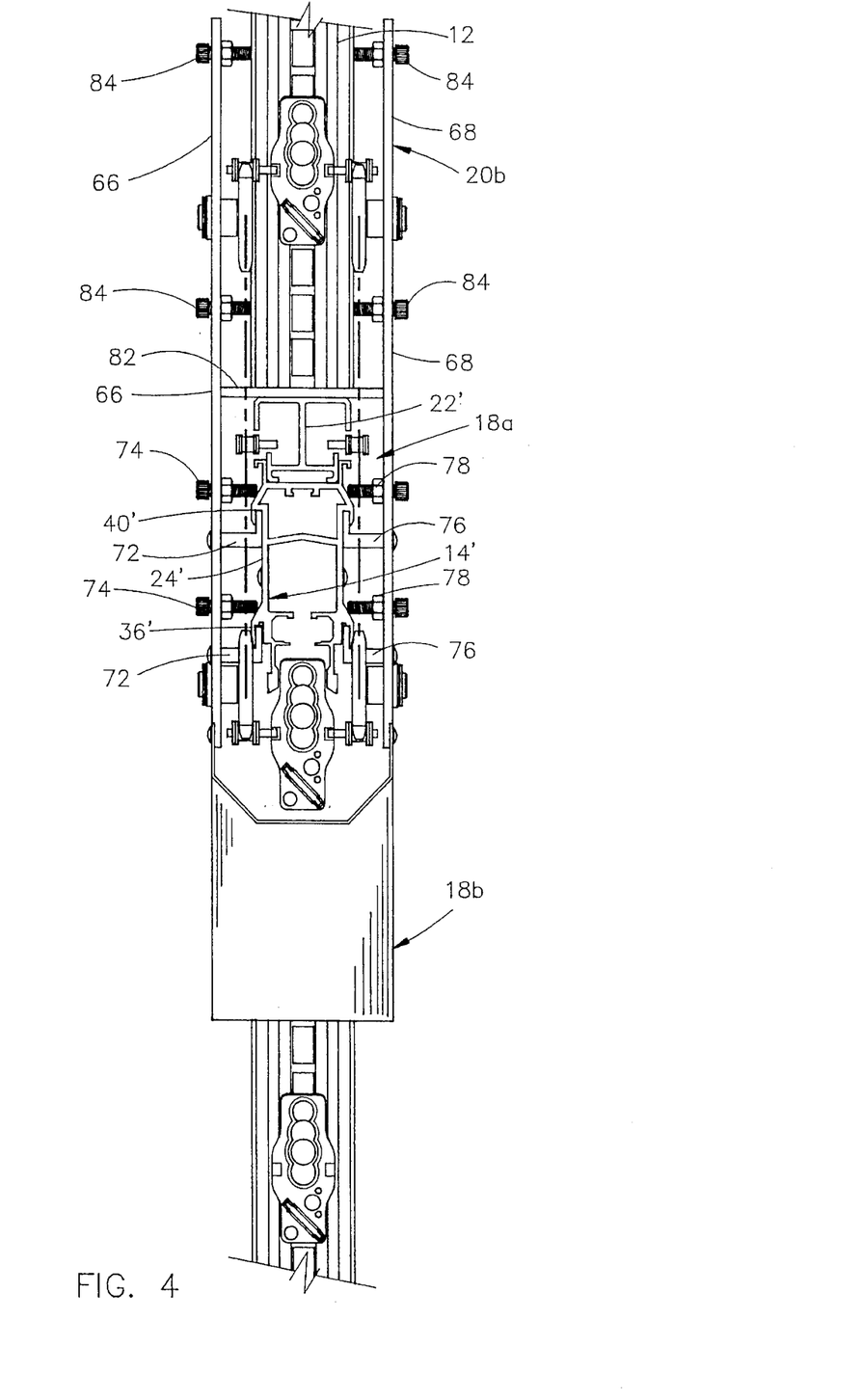
FIG. 4 is a top elevational view of the elevator with the top plate removed for clarity.

As shown in FIGS. 3 and 4, the vertical back 18a of lower housing 18 is formed from a length of conveyor track 14' attached to a length of support rail 22'. Top plate 46 of lower housing leg 18b has an aperture formed therein following the profile of track 14' and support rail 22', such that back 18a is fastened within housing 18b with screws 58, with track 14' projecting upwardly therefrom. A stop plate 58 is fastened to the lower end of track 14' and depends therefrom to stop movement of a specimen carrier 16 along lower track 14 in a position to permit engagement of lift pins 60 projecting from a pair of continuous loop chains 62, with projecting wings 64 on the specimen carrier 16, as described in more detail hereinbelow.

Referring once again to FIG. 1, upper housing 20 includes a general L-shaped forward plate 66, a matching rearward plate 68 and a top plate 70 connecting the upper ends of the forward and rearward plates 66 and 68. As shown in FIGS.

Figure 6:
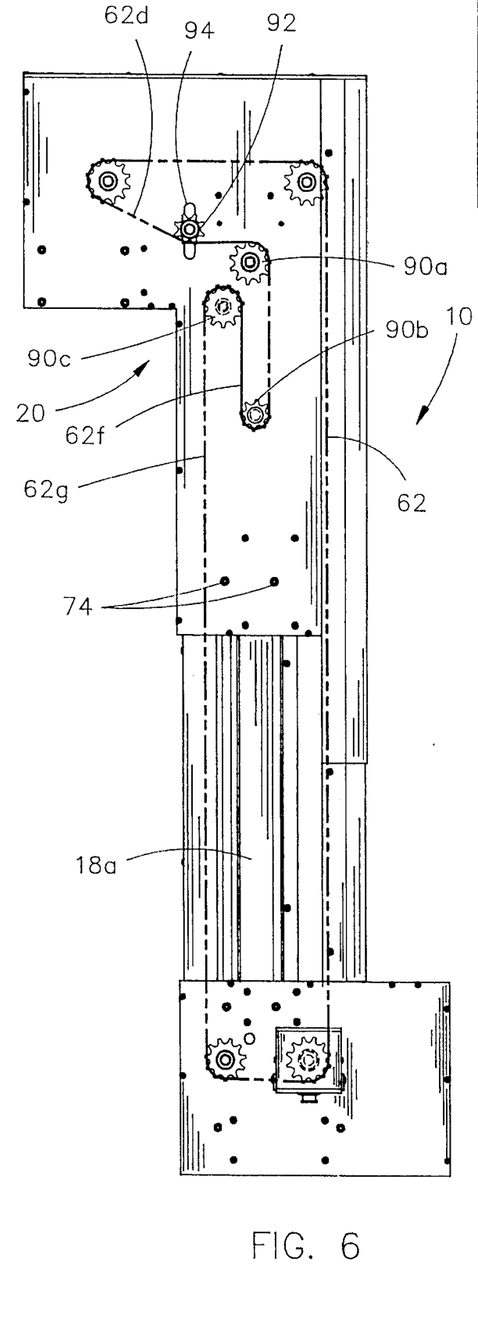
FIG. 6 is a front elevational view, with the elevator in a retracted position.
Figure 7:
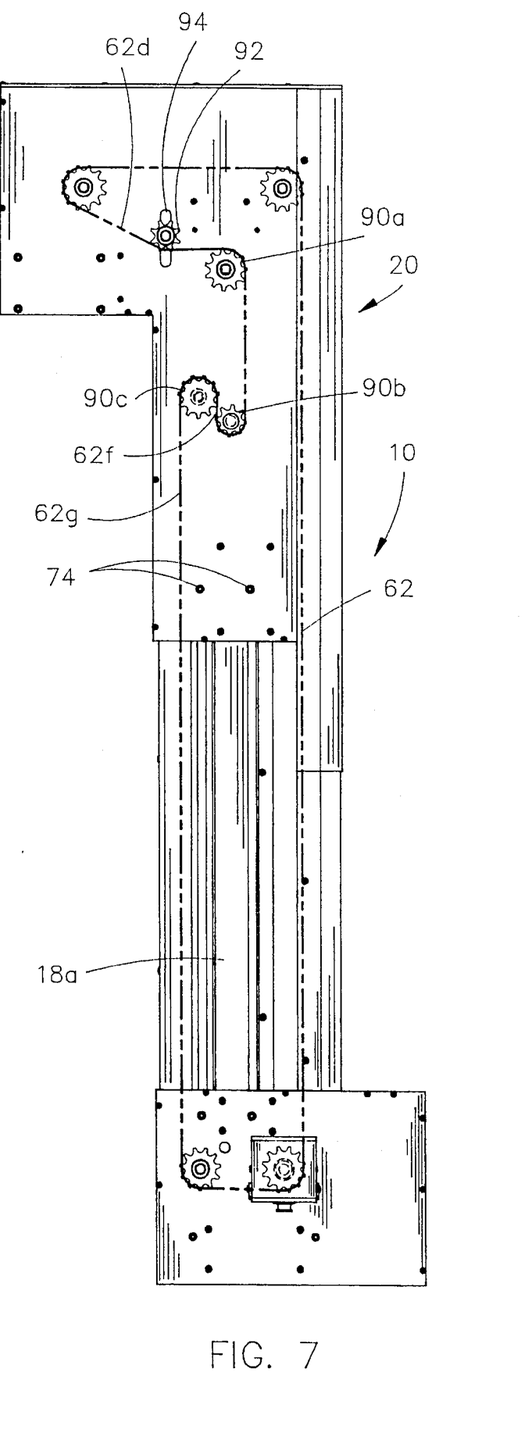
FIG. 7 is a front elevational view with the elevator in an extended position.
Figure 8:
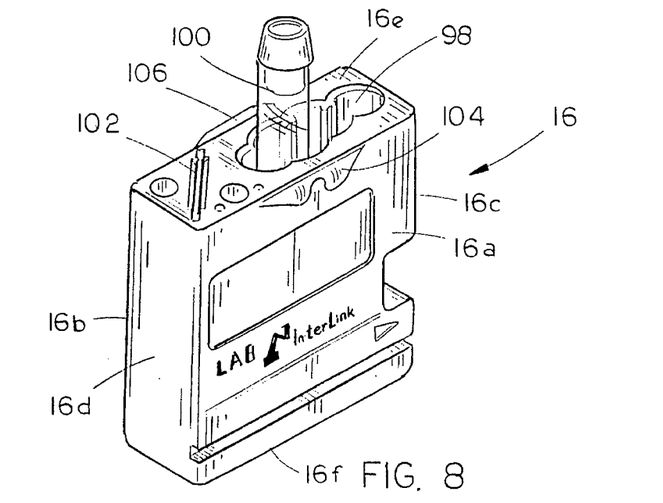
FIG. 8 is a perspective view of a specimen carrier used with the elevator.

4 and 5, a pair of hook members 72 are affixed to the inward face of forward plate 66 so as to engage the upper and lower channels 36' and 40' of track 14', with a pair of so screws 74 engaging the forward leg 24' to secure upper housing 20 in the desired position along track 14'. A pair of opposing hook members 76 and set screws 78 are mounted through rearward plate 68 in a similar fashion to selectively engage the rearward leg 26' of track 14'. FIGS. 6 and 7 show the overall height of elevator 10 adjusted between a Shorter height and longer height, to meet the particular requirements of the vertical spacing of a pair of vertically spaced conveyor tracks. By loosening and tightening set screws 74, upper housing 20 may be selectively secured at the desired location along lower housing back 18a.

Figure 5:
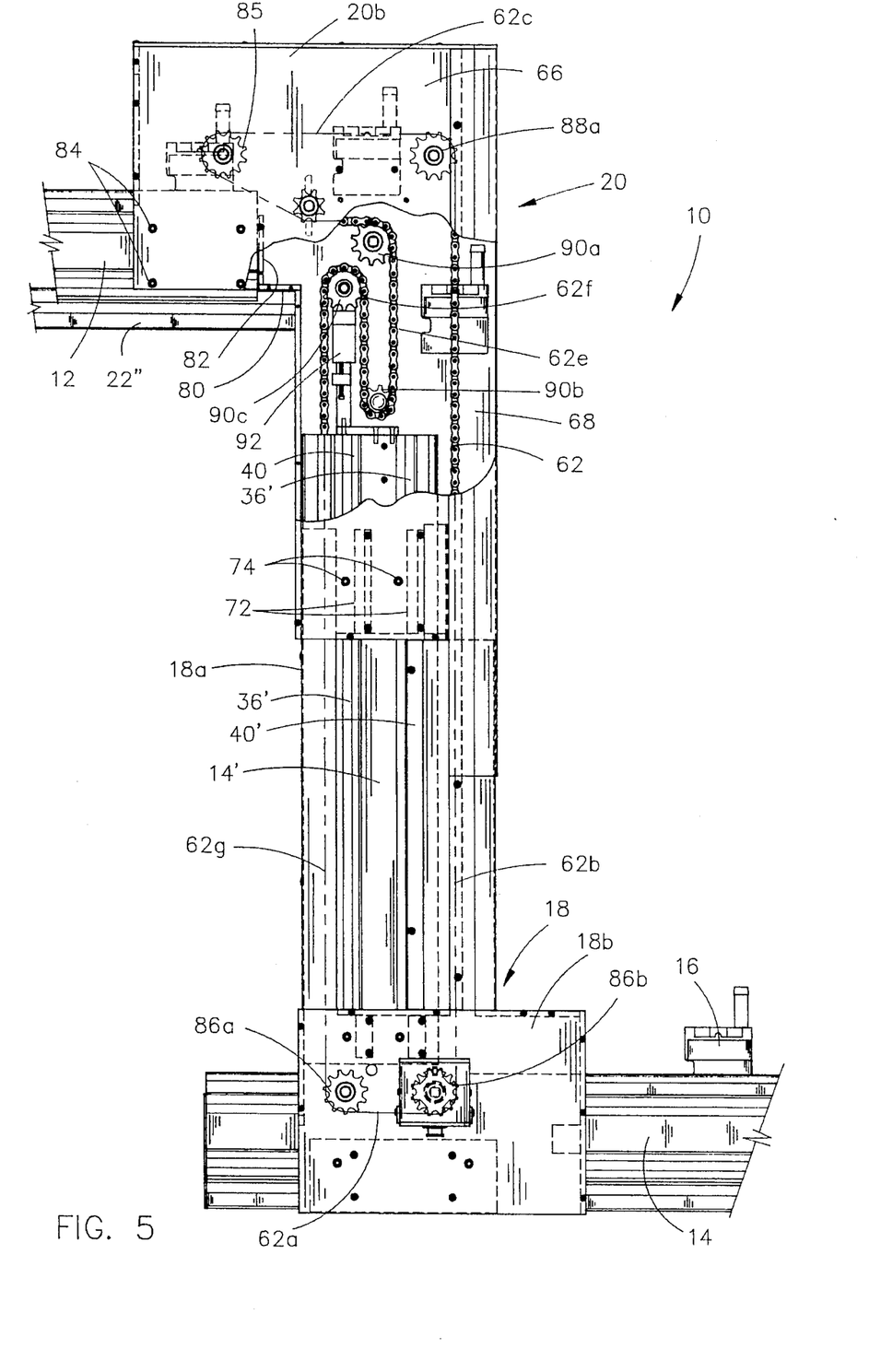
FIG. 5 is a front elevational view, with portions broken away.

Referring to FIG. 5, it can be seen that upper housing 20 includes a horizontally oriented support plate 80 affixed between the forward and rearward plates 68, on the bottom of the projecting leg 20b of housing 20. Support plate 80 rests on the support rail 22" of upper conveyor track 12. As shown in FIG. 5, support rail 22" projects beyond the end of upper conveyor track 12 specifically to accept support of upper housing 20 of elevator 10. A stop plate 82 projects vertically between forward and rearward plates 66 and 68 of upper housing 20 and is oriented to contact the end of upper conveyor track 12, when properly positioned within upper housing 20 of elevator 10.

As shown in FIG. 4 and 5, upper housing 20 is secured to upper conveyor track 12 by set screws 84 extending through forward and rearward plates 66 and 68 and biasing against the opposing sides of track 12.

The endless loop chains 62 are engaged around a plurality of pairs of sprockets in order to raise or lower a specimen carrier 16 between upper and lower conveyor tracks 12 and 14. Since each sprocket shown in FIG. 5 has an opposing coaxial sprocket associated therewith, only one set of sprockets will be described in detail herein. A pair of lower sprockets 86a and 86b are rotatably mounted within lower housing leg 18b and preferably horizontally spaced apart from one another. Chain 62 includes a first horizontal leg extending beneath lower sprocket 86a and thence around lower sprocket 86b and a second leg 62b extending vertically upwardly from lower sprocket 86b to the first of a pair of upper sprockets 88a and 88b. Sprockets 88a and 88b are rotatably mounted and horizontally spaced apart in the leg 20b of upper housing 20, with a third leg 62c of chain 62 extending from sprocket 88a to sprocket 88b. A pair of intermediate sprockets 90a and 90b are vertically spaced apart from one another and located below upper sprockets 88a and 88b and are mounted in upper housing 20. A third intermediate sprocket 90c is rotatably mounted on an upright 92 which projects upwardly from the upper end of lower housing back 18a. A fourth leg 62d of chain 62 extends from upper socket 88b, and around the upper sprocket 90a of intermediate sprockets 90a and b. A fifth leg 62e of chain 62 extends vertically downwardly from sprocket 90a to sprocket 90b, thence upwardly to form sixth leg 62f, and around third intermediate sprocket 90c. The seventh leg 62g of chain 62 extends vertically from third intermediate sprocket 90c downwardly to the first lower sprocket 86a, to complete the loop.

Referring now to FIGS. 6 and 7, it can be seen that the adjustment of vertical height of elevator 10 is accomplished by the use of intermediate sprockets 90a, 90b and 90c. By locating third intermediate sprocket 90c vertically between sprockets 90a and 90b, with third sprocket 90c connected to the lower housing 18 and sprockets 90a and 90b connected to the upper housing 20, the lengths of legs 62f and 62g of chain 62 will be inversely proportional, so as to maintain the overall length of chain 62. A tension pulley 92 is adjustably mounted in a slot 94 to provide a biasing force against leg 62d of chain 62, to maintain tension throughout the chain loop 62. As shown in FIG. 1, a drive motor 96 is connected to sprocket 90a in order to drive the chains 62 about the system.

Referring now to FIGS. 8–11, a specimen carrier 16 is shown in more detail. Specimen carrier 16 is preferably formed of a solid block of plastic material, with forward and rearward faces 16a and 16b, right and left ends 16c and 16d, and top and bottom surfaces 16e and 16f. A cavity 98 is provided for retaining a specimen tube 100 in a generally upright orientation, and a generally rectangular slot 102 is provided for retaining a specimen slide in specimen carrier 16. A pair of wings 104 and 106 project outwardly in opposite directions from the forward and rearward faces 16a and 16b respectively, and are located adjacent the top surface 16e of specimen carrier 16. Wings 104 and 106 are identical, and therefore only wing 104 will be described in detail herein.

Figure 9:
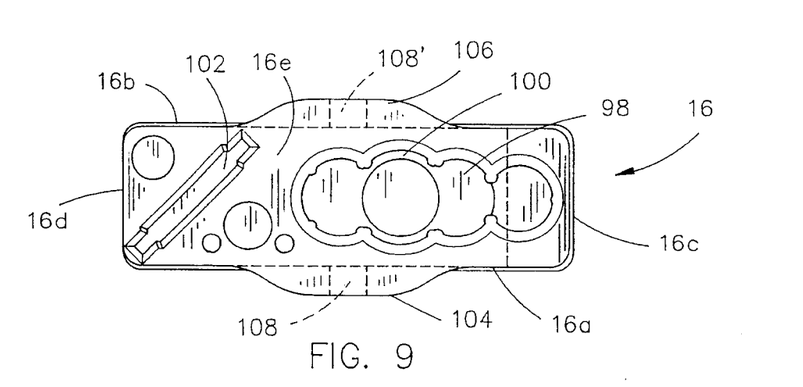
FIG. 9 is a top elevational view of the specimen carrier.
Figure 10:
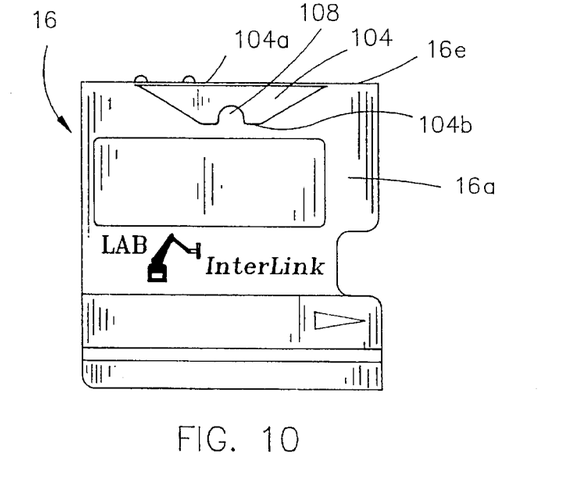
FIG. 10 is a front elevational view of the specimen carrier.
Figure 11:
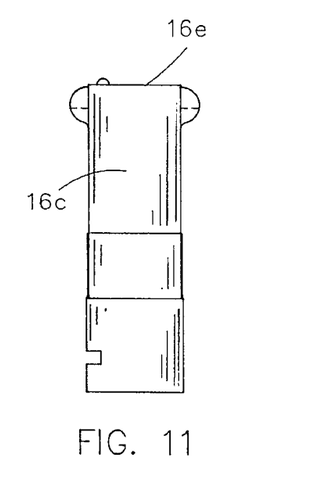
FIG. 11 is an end elevational view taken from the right side of FIG. 10.

Referring now to FIG. 10, wing 104 includes an upper surface 104a, and a lower surface 104b, each projecting outwardly from forward face 16a of carrier 16. A generally semicylindrical notch 108 is formed in lower surface 104b and extends orthogonally from forward face 16a of carrier 16, to receive lift pins 60 therein. Preferably, lower surface 104b slopes upwardly towards carrier top surface 16d from diametric sides of notch 108, to form a generally inverted triangular shape, as shown in FIG. 10. As shown in FIG. 9, wings 104 and 106 project outwardly from forward and rearward faces 16a and 16b, and are centered between ends 16c and 16d. Preferably, wings 104 and 106 have a length less than the full length of forward and rearward faces 16a and 16b. A corresponding notch 108' is formed in wing 106, as shown in FIG. 9.

Whereas the invention has been shown and described in connection with the preferred embodiment thereof, many modifications, substitutions and additions may be made which are within the intended broad scope of the appended claims.

I claim:

1. An elevator for moving a specimen carrier between vertically spaced apart conveyor tracks, comprising:

an elevator having an upper housing removably connected to an upstream end of an upper conveyor track and having a lower housing removably connected to a downstream end of a lower conveyor track;

each said conveyor track having a moving support surface for transporting a specimen carrier downstream, and a pair of arms projecting upwardly on opposing sides the support surface for guiding a specimen carrier;

said elevator including means for lifting a specimen carrier vertically off of the downstream end of the lower track and placing a lifted specimen carrier on the upstream end of the upper track;

said means for lifting and placing a specimen carrier including:

a pair of opposing, spaced apart, coaxial lift members operably mounted to move in a continuous loop between the lower track downstream end and upper track upstream end; and each specimen carrier including opposingly disposed wings cooperable with the lift members to selectively receive opposing free ends of the lift members:

a pair of continuous loop chains engaged around a plurality of pairs of spaced apart, coaxial sprockets;

a drive motor operably connected to a pair of drive
   sprockets engaged with said pair of chains to selectively drive the same;

said pair of lift members including one lift member
   attached to one of said pair of chains, and the opposing
   lift member attached to the second of said pair of
   chains;

a first sprocket pair rotatably mounted in the lower
   housing on opposing sides of the lower conveyor track;

said pair of chains forming a chain loop with a first leg
   extending between the first sprocket pair and a second
   sprocket pair;

a stop plate mounted over the support surface of the lower
   conveyor track and located to stop a specimen carrier
   on the lower track transport surface with the specimen
   carrier's wings aligned vertically with the first leg of
   the chain loop to receive the lift members;

a second sprocket pair rotatably mounted in the upper
   housing directly above the first sprocket pair, such that
   the first leg of the chain loop is generally vertical;

a third sprocket pair rotatably mounted in the upper
   housing on opposing sides of the upper conveyor track,
   and spaced horizontally from the second sprocket pair;

said chain loop having a second leg extending from the
   second sprocket pair to the third sprocket pair;

said third sprocket pair located to place a specimen carrier
   carried on the chain loop on the transport surface of the
   upper track.

2. The elevator of claim 1, wherein said upper and lower housing back end selectively and slidably connected in vertical alignment to permit adjustment of the distance between the upper and lower housing legs.

3. The elevator of claim 2 wherein said upper housing includes forward and rearward spaced apart and parallel plates, said upper track upstream end connected to said elevator within the upper housing leg between said plates; and wherein said lower housing includes forward and rearward spaced apart and parallel plates, said lower track downstream end connected to said elevator within the lower housing leg, between said plates.

4. The elevator of claim 3, further comprising:

first and second intermediate sprocket pairs aligned vertically and vertically spaced apart and rotatably mounted in said upper housing; and a third intermediate sprocket rotatably mounted to the lower housing and vertically located between the first and second intermediate sprockets, and spaced horizontally therefrom;

said third intermediate sprocket mounted for adjustable movement with the lower housing relative to the upper housing;

said chain loop extending from the third sprocket pair, around the first intermediate sprocket, thence downwardly around the second intermediate sprocket, thence upwardly around the third intermediate sprocket, and thence to the first sprocket.

* * * * *